United States Patent
Freger et al.

(10) Patent No.: US 6,954,662 B2
(45) Date of Patent: Oct. 11, 2005

(54) METHOD OF MONITORING GLUCOSE LEVEL

(75) Inventors: David Freger, Ashkelon (IL); Avner Gal, Hertzeliya (IL); Alexander M. Raykhman, East Greenwich, RI (US)

(73) Assignee: A.D. Integrity Applications, Ltd., Ashkelon (IL)

(*) Notice: Subject to any disclaimer, the term of this patent is extended or adjusted under 35 U.S.C. 154(b) by 226 days.

(21) Appl. No.: 10/643,804

(22) Filed: Aug. 19, 2003

(65) Prior Publication Data

US 2005/0043602 A1 Feb. 24, 2005

(51) Int. Cl.$^7$ ................................ A61B 5/00
(52) U.S. Cl. .................... 600/316; 600/365; 600/347
(58) Field of Search ................ 600/309–310, 600/365, 316, 322, 347; 128/920

(56) References Cited

U.S. PATENT DOCUMENTS

| | | | |
|---|---|---|---|
| 5,050,612 A | 9/1991 | Matsumura | |
| 5,119,819 A | 6/1992 | Thomas | |
| 5,657,754 A | 8/1997 | Rosencwaig | |
| 5,666,956 A | 9/1997 | Buchert | |
| 5,752,512 A | 5/1998 | Gozani | |
| 5,771,891 A | 6/1998 | Gozani | |
| 5,792,668 A | 8/1998 | Fuller | |
| 5,795,305 A | 8/1998 | Cho | |
| 5,924,996 A | 7/1999 | Cho | |
| 5,941,821 A | 8/1999 | Chou | |
| 6,049,728 A | 4/2000 | Chou | |
| 6,070,093 A * | 5/2000 | Oosta et al. | 600/316 |
| 6,150,812 A | 11/2000 | Pinsky | |
| 6,226,541 B1 | 5/2001 | Eppstein | |
| 6,309,352 B1 | 10/2001 | Oraevsky | |
| 6,322,963 B1 | 11/2001 | Bauer | |
| 6,342,347 B1 | 1/2002 | Bauer | |
| 6,377,828 B1 | 4/2002 | Chaiken | |
| 6,405,069 B1 | 6/2002 | Oraevsky | |
| 6,882,940 B2 * | 4/2005 | Potts et al. | 600/347 |
| 2003/0130616 A1 * | 7/2003 | Steil et al. | 600/365 |

\* cited by examiner

*Primary Examiner*—Eric F. Winakur
*Assistant Examiner*—Matthew Kremer
(74) *Attorney, Agent, or Firm*—Lilling & Lilling PC

(57) ABSTRACT

The method of monitoring or measuring the concentration of glucose level in human and animal blood uses a non-invasive technique and includes measurements of the speed of sound through the blood, the conductivity of the blood, and the heat capacity of the blood, or by non-invasive measurement of any other parameters that can be used to calculate the glucose level. Thereafter, the glucose level for each of the three measurements is calculated and the final glucose value is determined by a weighted average of the three calculated glucose values.

19 Claims, 5 Drawing Sheets

METHOD OF MONITORING GLUCOSE LEVEL

FIELD OF THE INVENTION

This invention relates to medicine and the treatment of specified diseases and, in particular, to a method of monitoring the glucose level in human and animal blood using a non-invasive technique.

BACKGROUND OF THE INVENTION

As is well known in medical circles, one of the more important blood components to measure for diagnostic purposes is glucose, especially for diabetic patients. The well-known and typical technique for determining blood glucose concentration is to secure a blood sample and apply that blood to an enzymatically medicated colorimetric strip or an electrochemical probe. Generally, this is accomplished from a finger prick. For diabetic patients who may need to measure blood glucose a few times a day, it can immediately be appreciated that this procedure causes a great deal of discomfit, considerable irritation to the skin and, particularly, the finger being pricked, and, of course, infection.

For many years, there have been any number of procedures for monitoring and measuring the glucose level in humans and animals. These methods, however, generally involve invasive techniques and, thus, have some degree of risk, or at least some discomfit, to the patient. Recently, some non-invasive procedures have been developed, but still they do not always provide optimum measurements of the blood glucose. At present there is no practical, confirmed solution.

Thomas (U.S. Pat. No. 5,119,819) teaches a non-invasive method of monitoring blood glucose, but it is based on only an acoustic velocity measurement based on the two-way travel time of an ultrasound pulse.

Gozani (U.S. Pat. No. 5,771,891) discloses a non-invasive method for blood analyte measurement. First, there is electrical stimulation of an endogenous tissue and then the detection of the resulting electrical response to the stimulus. One embodiment shows electrical stimulation of a hypoxic peripheral nerve, and then the detection of the resulting Compound Action Potential elsewhere along the nerve.

Cho (U.S. Pat. Nos. 5,795,305 and 5,924,996) uses combined temperature and measurements of either infrared radiation or thermal conductivity to determine the glucose concentration.

Chou (U.S. Pat. Nos. 5,941,821 and 6,049,728) determines the blood glucose by a photoacoustic measurement in which the acoustic pulse is generated by heating the patient's skin with electromagnetic radiation.

In each of these prior art techniques, only one (or in one case two) parameters are measured. Thus, the possibility of an error is increased. The instant invention uses measurements of three distinct parameters to determine the blood glucose level, thereby substantially increasing the accuracy of the measurement. Moreover, none of the prior art techniques utilize any measurement of electrical conductivity and heat capacity, which are two of the parameters measured in the instant invention.

Therefore, there is a need for a more accurate non-invasive procedure for measuring glucose level, by means of monitoring multiple parameters.

SUMMARY OF THE INVENTION

This and other objects of the invention are effected by a method of monitoring or measuring the concentration of glucose level in human and animal blood using a non-invasive technique, which includes simultaneous measurements using two, three or more different technologies, which support each other, in order to achieve a more precise and reliable result. The method uses any combination of the three technologies, as follows:

Measuring the speed of sound through the blood, while inside the body,

Measuring the conductivity of the blood, by means of electromagnetic inductance, Measuring the heat capacity of the blood, by means of changing the temperature of the measured volume.

Preferably, these measurements may be made, for example, through the ear-lobe.

By determining three physical properties of a patient's blood, the concentration of glucose in the blood can be inferred. The specific physical properties that need to be measured are acoustic velocity, electrical conductivity and heat capacity.

The method can be used for:

1. Single test, using two or three technologies, or
2. Continuous test, using one, two or three technologies, or
3. A combination of (1) and (2) above.

DETAILED DESCRIPTION OF THE INVENTION

Figure 1:
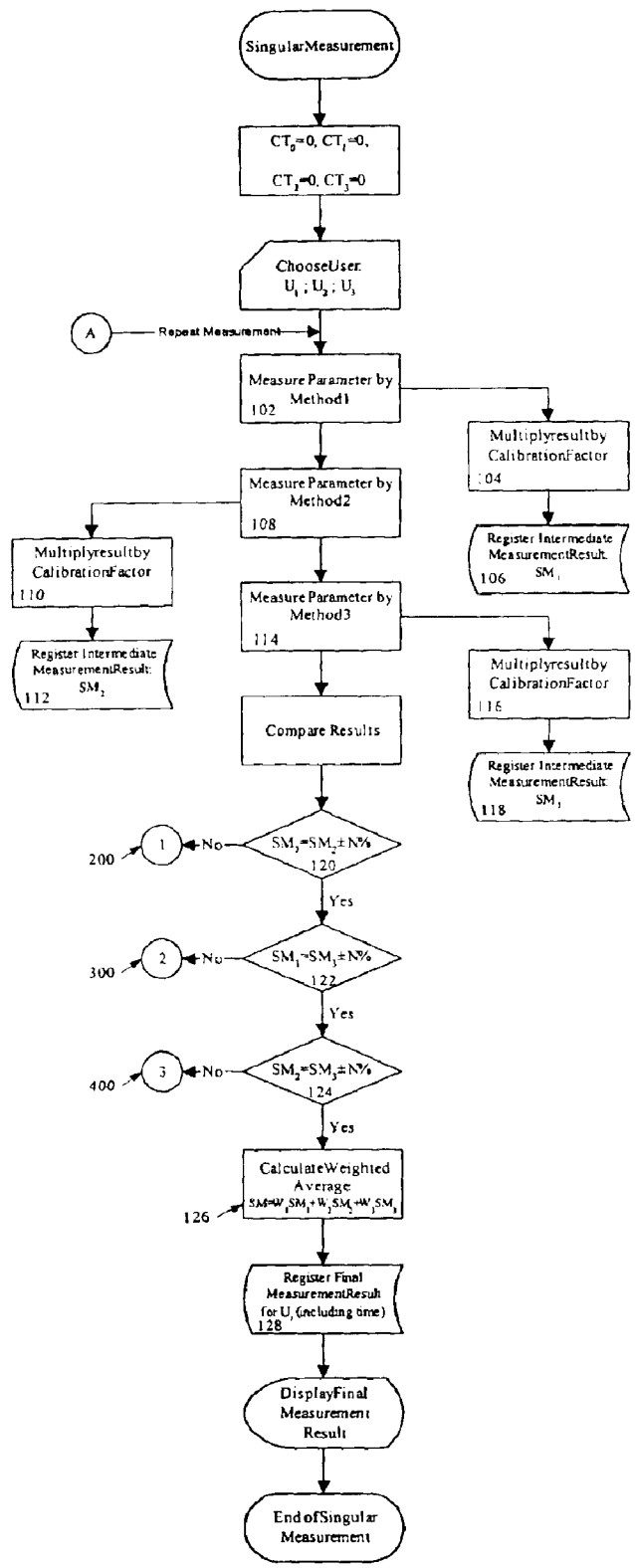
FIGS. 1–4 are a flow chart showing the method of determining the glucose level with single measurements of each parameter.
Figure 2:
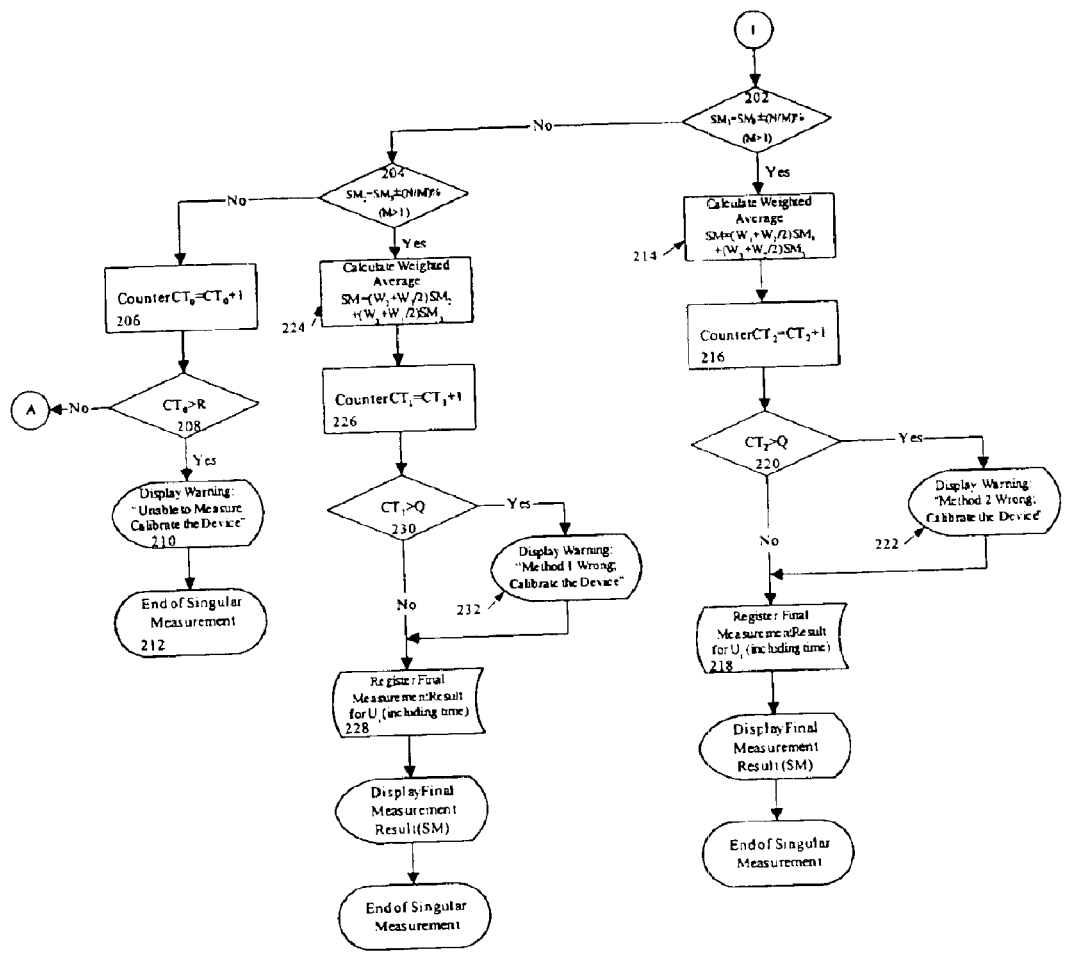
Figure 3:
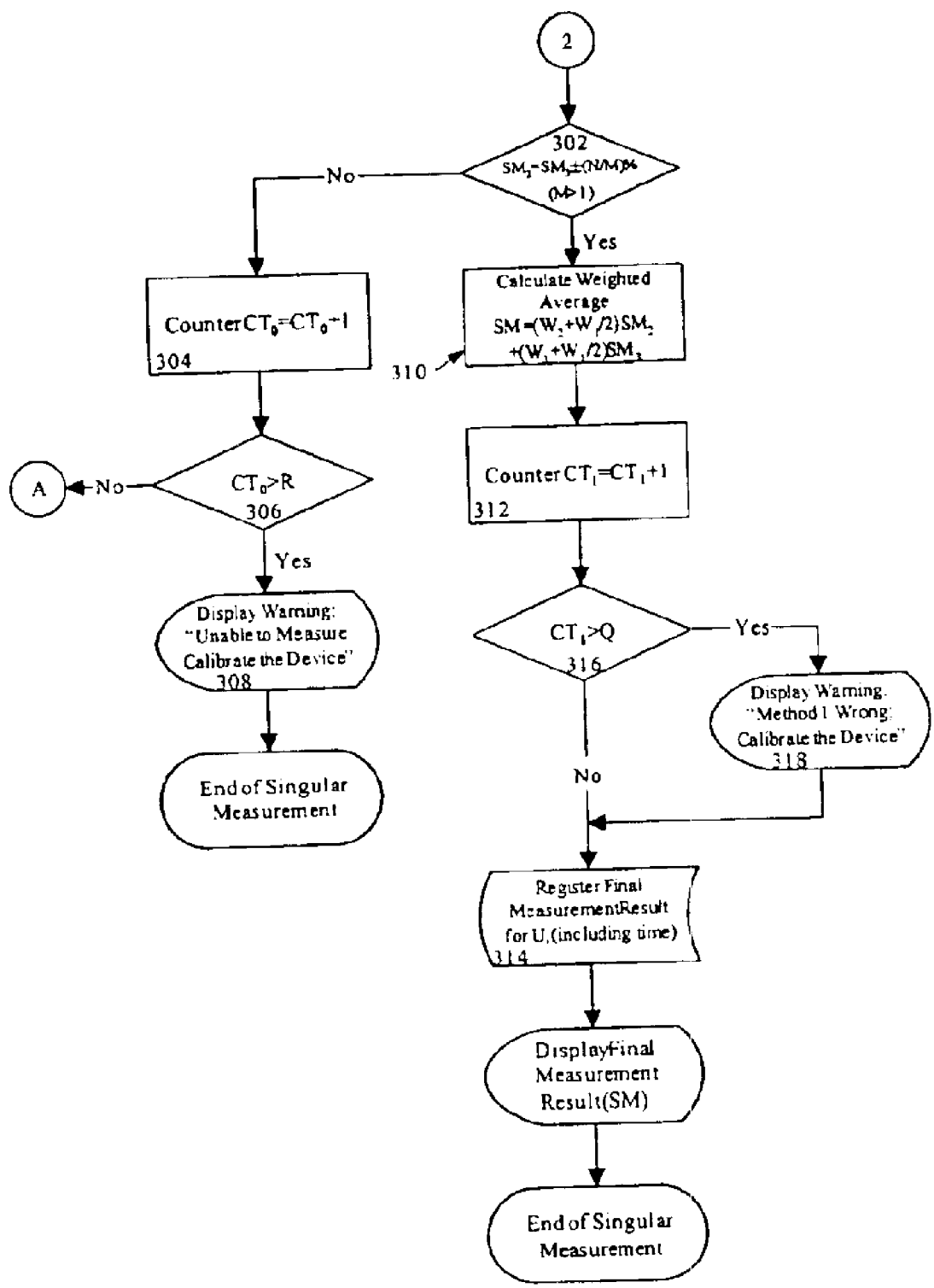
Figure 4:
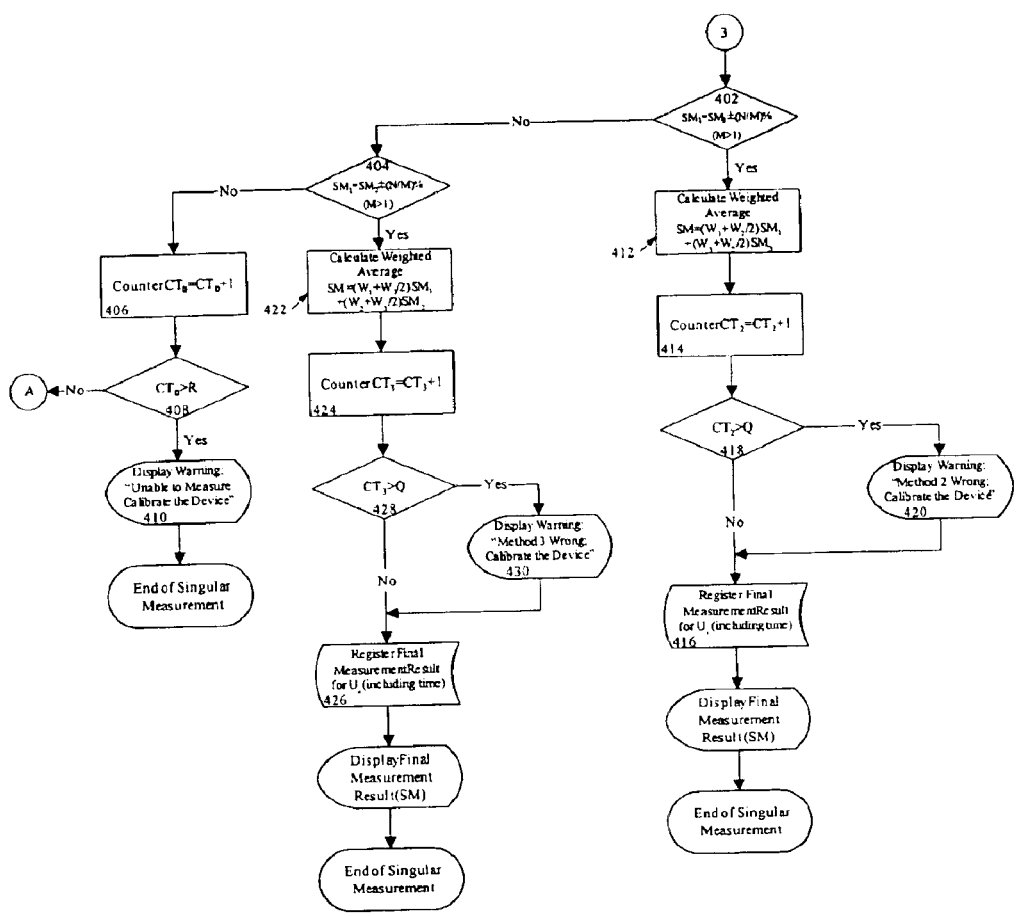

The measurement concept is based on three technologies: speed of sound through blood, conductivity of the blood and heat capacity of the blood. In particular, the method utilizes a combination of any one of the three technologies, simultaneously or sequentially.

Firstly, there is a determination of:

the speed of sound through the blood, while inside the body, the conductivity of the blood, by means of electromagnetic inductance, and the heat capacity of the blood, by means of changing the temperature of the measured volume.

Preferably, these measurements may be made, for example, through the ear-lobe. Thereafter, based on the thus obtained parameters, the glucose level is calculated.

In Single Measurement Mode (SM), the device starts the measurement sequence, using the three methods. The different results are analyzed and compared, as described hereunder, in order to sum up the data and display as well the combined result.

In Continuous Measurement Mode (CM), the device starts as in SM, using the three methods. The following routine measurements are based on a single method, and done repeatedly in preset intervals. Once every few measurements, or every certain period of time, the device makes, automatically, a detailed measurement, based upon all three measurements, and calibrates itself. This method is used also in order to bias the following results.

The results of the different measurements are checked against a predetermined tolerance window, which checks the reliability of the combined result. Once the different results meet the tolerances, the end result is the weighted average of all the single measurements. When the deviation of one or more of the measurement results is out of the tolerance window, then the method first checks, according to a tree of choices, whether the deviation is acceptable, and if it is, it gives a final result. If the deviation is not acceptable, the method dictates the starting of a new measurement session. Such a case occurs also if all the results are out of tolerance.

In the mode of continuous measurement, when a single technology is used, a combined measurement is done, automatically, at certain preset time intervals, in order to compensate for drifts, and to recalibrate the result.

The speed of sound through the blood is related to the concentration of the glucose within the blood. An ultra sound signal is transmitted, for example, via the ear lobe, hits an acoustic short in the other side and returns to a receiving element. Based on the measurements, the glucose level is then calculated in a known manner.

Further, the level of conductivity is a function of the glucose level within the blood. An electromagnetic signal with known parameters is induced, for example, against the ear lobe, while the current level, caused by the inductance, depends on the glucose level. The current amplitude is measured, and analyzed, in order to conclude the Glucose level.

The heat capacity of a solution, blood in our case, is a function of its ingredients. A known amount of energy is applied, for example, to the ear lobe, and causes a change in its temperature. The intensity of the gradient is a function of the glucose level, since it is the dominant varied ingredient. This intensity is measured, in order to correlate it with the glucose level.

Once the speed, conductivity and heat capacity are determined, the glucose level is calculated based on the measurements of each of the three parameters. Then, the three glucose values are evaluated to see if all three values are the same within a stated tolerance level. If they are, the glucose level is finalized based on a weighted average of the three glucose values. In the event one result is out of tolerance, then the other two are checked against a tighter tolerance; and, if they both meet it, then the final result is calculated.

It may also be appreciated that the advantage of the invention is achieved by measuring three parameters, instead of just one as the prior art generally does, and then checking to see if the measurements are within certain tolerances, followed by calculating a weighted average. It is for only illustrative purposes that mention is made of the specific parameters, i.e. speed of sound, conductivity and heat capacity. If non-invasive measurements of other parameters were used and the results were checked to ensure they were within acceptable tolerances, followed by calculating the weighted average, this too would come within the scope of the invention. In this manner, the method of the invention would work precisely the same. Among the other parameters that can be measured in a non-invasive manner are: acoustic impedance, electrical/magnetic coefficient, thermal conductivity, elasticity, blood density, specific gravity, polarization coefficient, optical scattering, nuclear magnetic resonance, analyte, blood and body temperature, the effects of thermal waves, the infrared radiation naturally emitted from the body, responses by the tissue to a stimulus, and electrical properties, such as electromotive force or current. Thus, the invention contemplates using not just the measurements of speed of sound, conductivity and heat capacity, but even just one or two of these parameters along with measurements of one or two other parameters, or even using three other parameters entirely. The essence of the invention is non-invasive measurements of 3 parameters, and it is not material which parameters are used, so long as they are parameters from which the glucose level can be determined.

The method has two operational modes: singular and continuous measurements. In the singular mode, a single measurement is taken (for all three methods). If the results are within a pre-determined tolerance window, than the measurements are finished, otherwise, the process is repeated. In the continuous mode, the first measurement is done by using all three methods, and then, repeatedly, only a single technology (for example, just the acoustic) is used, in order to measure the trend, based on the first (combined) measurement as a reference. The rate is predetermined by the user (if he prefers a period other than the default), and can be preset, for example, between 10 minutes to 2 hours or so. In the continuous mode, every constant period of time (probably in the order of two hours or so), or after a predetermined number of measurements are taken, a self calibration process is done, by (automatically) using all three technologies, and biasing the results to a more precise one.

Tolerances may be determined in one of two manners. One way is a comparison between the results of the different measurements and checking the deviation in between, to be limited to a certain percentage (probably in the order of 10% or 15% or so). A second way is checking the deviation between each result and the previous one. In this case the deviation level is a function of the time between measurements. Orders here may vary between about 20% for a short period of time, to about 50% (and even more) for a longer period.

For Singular Measurement, the method requires independent measurements of the 3 different parameters. Each result is multiplied by its relevant calibration factor (calculated off line), in order to bring all the results to the same measured units (namely: mg/dl). Then, the results are compared. If all three results are similar, within a certain tolerance window (for example: Result 1=Result 2±10%, and Result 2=Result 3±10%, and Result 1=Result 3±10%), then the weighted average final result will be calculated as: Final Result= (Result 1×Relative Weight 1)+(Result 2×Relative Weight 2)+(Result 3×Relative Weight 3). If only 2 measurements give similar results, while the third one is out of the tolerance window, then the algorithm checks if the two similar results are within a narrower tolerance window (for example, 5%). If this is the case, the final result will be the weighted average of these two results, while a counter (relating to the third method) will increase its state by one. When the counter reaches a certain limit, a warning to the user is displayed, notifying of the problem in the particular method, and asks the user to recalibrate. In cases where the three methods give different readings (all three are out of the wide tolerance window, or one out of the wide window and two out of the narrow window), the method automatically (without any involvement of the user) repeats the measurement. If the problem repeats for more then a certain amount of times, the routine warns about the inability of measuring, and asks the user to recalibrate.

The weight for each measurement depends on the reliability of the specific measurement procedure. These figures generally would be determined during clinical tests. In situations where the 3 measurement procedures are all equally reliable, then the weighted factors would be identical, and equal to $\frac{1}{3}$ (0.333 . . . ). The purpose of the "relative weight" variable is to take into consideration the fact that in some situations one measurement may be more accurate than another due to the specific measurement procedure being used. For example, if one measurement is more reliable than the others, it can be given a higher weight (for example, 0.5), while the others will receive (for example) 0.2 and 0.3 (the total sum of the weights should sum up to 1, or 100%). By way of example, assuming that all methods gave the same reading (say, 95 mg/dl), therefore the final result will be: 0.5×95+0.2×95+0.3×95=95.

Whenever a legitimate result is present, the method registers the result, under the file of the present user, together with date and time of the result, and displays the result on a user's screen.

For Continuous Measurement, the user dictates the amount of measurements between Auto-Calibration, and measurements are done repeatedly, using a single (constant) method, at a preset rate. Every time the measurements amount pass the preset figure, a full measurement is done, using all three methods, as in the singular measurement case. The same idea of registering and displaying results is used in this process.

In FIGS. 1–4, there is a flowchart to illustrate the Singular Measurement procedure. First (see FIG. 1), one of the measurements is made 102, for example, of the speed of sound, but it could be any parameter that is measured in an non-invasive manner. Then, it is multiplied by any necessary calibration factor 104 and then in some manner this value of the glucose level 106 is recorded. This procedure is repeated for the other measurements, i.e. electrical conductivity and heat capacity or any other selected parameters that can be measured by non-invasive means, so that there is a value for each of the three parameters (steps 108–112 and 114–118).

At this point the routine checks to determine if the glucose measurement of the first parameter is within an acceptable deviation of the glucose measurement of the second parameter 120. If it is, then it checks to determine if the glucose measurement of the first parameter is within an acceptable deviation of the glucose measurement of the third parameter 122. In the event that these two values are also close enough, then the routine checks to determine if the glucose measurement of the second parameter is within an acceptable deviation of the glucose measurement of the third parameter 124.

(Hereinafter, for easy of terminology in describing the flowchart, when the term "first measurement" is use it means "glucose measurement of the first parameter," and similarly for the second and third measurements.)

Upon determining that all three measurements are within acceptable variations of each other, the weighted average is calculated 126. This provides the user with the final value of the glucose level, which may then be recorded in any suitable manner for future reference 128. This would conclude the single measurement procedure.

In the event the routine checks determines the first measurement is not within an acceptable deviation of the second measurement 200, then (see FIG. 2) the routine checks to see if the first measurement is within an acceptable tighter deviation from the third measurement 202. If they are not, now the second and third measurements are compared to determine if the second measurement is within the acceptable tighter deviation of the third measurement 204. In the event that these two measurements are also not within acceptable limits, there is a situation where none of the three measurements are within an acceptable deviation of the other two measurements and the measurements cannot be used. A counter is incremented by one to record the unsuccessful procedure 206. If a predetermined number of failed routines has not been reached 208, the routine returns to the beginning (A) and repeats the entire procedure. If the predetermined number of unsuccessful routines is shown by the counter, then, instead, the routine terminates 210 and the single measurement routine ends 212. A signal is then generated to the user to re-calibrate the measurement procedure for the entire routine.

In the event that when the routine determines the first measurement is not within an acceptable deviation of the second measurement, but (see FIG. 2) the routine then determines that the first measurement is within the acceptable tighter deviation from the third measurement, the weighted average is calculated with the second measurement being weighted as zero, while the other two measurements' weights are increased respectively (step 214). A counter is incremented to show that the second measurement deviated too much from the other measurements 216. This provides the user with the final value of the glucose level, which may then be recorded in any suitable manner for future reference 218. This would conclude the single measurement procedure. In the event that the counter now shows that there have been too many measurements of the second parameter which deviate by too much 220, a signal is generated to the user to re-calibrate the measurement procedure for the second parameter 222.

In the event that when the routine determines the first measurement is not within the acceptable deviation of the second measurement and the first measurement is not within the acceptable tighter deviation of the third measurement, but (see FIG. 2) the routine then determines that the second measurement is within the acceptable tighter deviation from the third measurement, the weighted average is calculated with the first measurement being weighted as zero, while the other two measurements' weights are increased respectively (step 224). A counter is incremented to show that the first measurement deviated too much from the other measurements 226. This provides the user with the final value of the glucose level, which may then be recorded in any suitable manner for future reference 228. This would conclude the single measurement procedure. In the event that the counter now shows that there have been too many measurements of the first parameter which deviate by too much 230, a signal is generated to the user to re-calibrate the measurement procedure for the first parameter 232.

In the event that, when the routine determines the first measurement is within the acceptable deviation of the second measurement, but the routine then determines that the first measurement is not within the acceptable deviation from the third measurement 300, then (FIG. 3) the routine checks to determine if the second measurement is within the acceptable tighter deviation of the third measurement 302. In the event that these two measurements are also not within acceptable limits, this is also a situation where none of the three measurements is within an acceptable deviation of the other two measurements and the measurements cannot be used. A counter is incremented by one to record the unsuccessful procedure 304. If a predetermined number of failed routines has not been reached 306, the routine returns to the beginning (A) and repeats the entire procedure. If the predetermined number of unsuccessful routines is shown by the counter 308, then, instead, the routine terminates and the single measurement routine ends. A signal is then generated to the user to re-calibrate the measurement procedure for the entire routine.

In the event that, when the routine determines the first measurement is within the acceptable deviation of the second measurement, but determines that the first measurement is not within the acceptable deviation from the third measurement, and then determines the second measurement is within the acceptable tighter deviation of the third measurement, the weighted average is calculated with the first measurement being weighted as zero, while the other two measurements' weights are increased respectively (step 310). A counter is incremented to show that the first measurement deviated too much from the other measurements 312. This provides the user with the final value of the glucose level, which may then be recorded in any suitable manner for future reference 314. This would conclude the single measurement procedure. In the event that the counter now shows that there have been too many measurements of the first parameter that deviated by too much 316, a signal is generated to the user to re-calibrate the measurement procedure for the first parameter 318.

In the event that when the routine determines the first measurement is within the acceptable deviation of both the second and third measurement, but determines that the second measurement is not within the acceptable deviation from the third measurement 400, the routine (FIG. 4) checks to determine if the first measurement is within the acceptable tighter deviation from the third measurement 402. If they are not, now the first and second measurements are compared to determine if the first measurement is within the acceptable tighter deviation of the second measurement 404. In the event that these two measurements are also not within acceptable limits, there is a situation where none of the three measurements are within an acceptable deviation of the other two measurements and the measurements cannot be used. A counter is incremented by one to record the unsuccessful procedure 406. If a predetermined number of failed routines has not been reached 408, the routine returns to the beginning (A) and repeats the entire procedure. If the predetermined number of unsuccessful routines is shown by the counter 410, then, instead, the routine terminates and the single measurement routine ends. A signal is then generated to the user to re-calibrate the measurement procedure for the entire routine.

In the event the routine determines that the first measurement is within the acceptable tighter deviation from the third measurement, the weighted average is calculated with the second measurement being weighted as zero, while the other two measurements' weights are increased respectively (step 412). A counter is incremented to show that the second measurement deviated too much from the other measurements 414. This provides the user with the final value of the glucose level, which may then be recorded in any suitable manner for future reference 416. This would conclude the single measurement procedure. In the event that the counter now shows that there have been too many measurements of the second parameter which deviate by too much 418, a signal is generated to the user to re-calibrate the measurement procedure for the second parameter 420.

On the other hand, if the first measurement is not within the tighter deviation from the third measurement, then the first measurement is compared to the second measurement to see if they are within the acceptable tighter deviation 404. If they are, the weighted average is calculated with the third measurement being weighted as zero, while the other two measurements' weights are increased respectively (step 422). A counter is incremented to show that the third measurement deviated too much from the other measurements 424. This provides the user with the final value of the glucose level, which may then be recorded in any suitable manner for future reference 426. This would conclude the single measurement procedure. In the event that the counter now shows that there have been too many measurements of the third parameter which deviate by too much 428, a signal is generated to the user to re-calibrate the measurement procedure for the third parameter 430.

Figure 5:
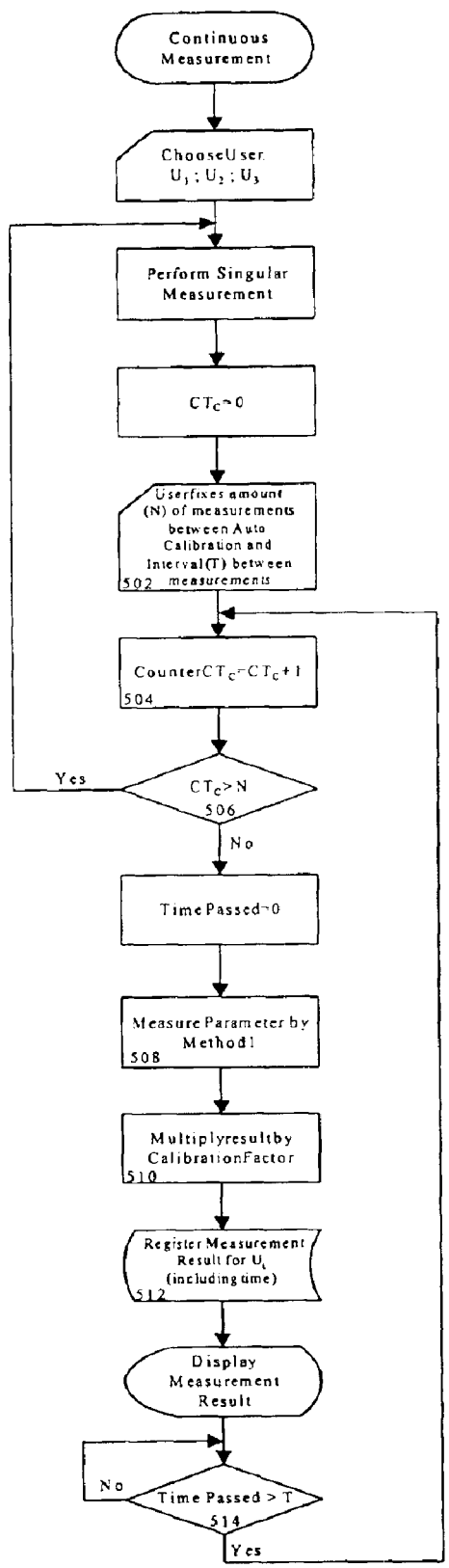
FIG. 5 is a flow chart showing the method of determining the trend of glucose level with continuous measurements of a single parameter.

FIG. 5 illustrates the procedure for Continuous Measurement. First, using the Single Measurement procedure, values are obtained for each of the three parameters. Then, the user must establish the number of measurements before auto-calibration and the interval between measurements (unless the user decides to use the prior numbers) 502.

Now, the counter increments itself by one 504. If the counter has now reached the number of measurements for auto-calibration 506, the current session of the Continuous Measurement routine ends and the routine goes back to the Single Measurement procedure, so that new values are obtained for each of the three parameters and a new Continuous Measurement session can begin.

If it is not time for auto-calibration, then the selected parameter (for example, the first parameter for speed) is measured 508. It is multiplied by a calibration factor 510 and the resulting glucose value is recorded in any suitable manner 512. At this point, the routine counts the time. When the proper time interval has occurred 514, the routine goes back to the beginning (step 504) and repeats the process.

The invention is described in detail with reference to a particular embodiment, but it should be understood that various other modifications can be effected and still be within the spirit and scope of the invention.

We claim:

1. A non-invasive method of determining the glucose level of blood in a patient comprising the steps of:
   a. non-invasively measuring the speed of sound through the blood of the patient;
   b. non-invasively measuring the electrical conductivity of the blood of the patient;
   c. non-invasively measuring the heat capacity of the blood of the patient;
   d. calculating the corresponding glucose level for each of the measurements of the speed of sound, electrical conductivity of the blood and heat capacity of the blood;
   e. comparing the three calculated glucose levels; and
   f. 1. if all three calculated glucose levels are similar within a predefined tolerance level, then calculating the final glucose level by determining a weighted average of the three calculated glucose levels; or
      2. if only two of the three calculated levels are similar within a predefined tolerance level, then calculating the final glucose level by determining a weighted average of only the two similar calculated glucose levels.

2. A non-invasive method of determining the glucose level according to claim 1, further comprising the steps of:
   g. repeating the measurement of one of the parameters of either speed, conductivity or heat capacity according to any one of the steps a–c herein;
   h. calculating the corresponding glucose level for the measurement of the parameter in step g herein; and
   i. periodically repeating steps a–f herein to confirm the accuracy of the glucose calculation.

3. A non-invasive method of determining glucose level according to claim 2, wherein steps a–f are repeated after a predetermined amount of time.

4. A non-invasive method of determining glucose level according to claim 2, wherein steps a–f are repeated after a predetermined number of measurements.

5. A non-invasive method of determining the glucose level according to claim 1, wherein the speed of sound is determined by means of measurements of an ultrasound signal transmitted through the body.

6. A non-invasive method of determining the glucose level according to claim 1, wherein the electrical conductivity of the blood is determined by means of electromagnetic inductance.

7. A non-invasive method of determining the glucose level according to claim 1, wherein the heat capacity of the blood is determined by means of changing the temperature of a measured volume.

8. A non-invasive method of determining glucose level according to claim 1, wherein the weight for each calculated glucose level is based on the reliability of the calculated glucose level's respective non-invasive measurement.

9. A non-invasive method of determining glucose level according to claim 1, wherein, if one of the calculated glucose levels is not within the predefined tolerance level, then checking the remaining two calculated glucose levels to confirm they are within a tighter tolerance range and then calculating the final glucose level by determining the weighted average of only the two similar calculated glucose levels.

10. A non-invasive method of determining glucose level according to claim 1, consisting of the additional steps of: incrementing a counter each time one of the calculated glucose levels is not within the tolerance level; and recalibrating measurement procedure when the counter indicates a predetermined number of times the calculated glucose level was not within the tolerance level.

11. A non-invasive method of determining the glucose level of blood in a patient comprising the steps of:
   a. non-invasively measuring three distinct parameters of the body from which glucose level can be calculated;
   b. calculating the corresponding glucose level for each of the three measurements;
   c. comparing the three calculated glucose levels; and
   d. 1. if all three calculated glucose levels are similar within a predefined tolerance level, then calculating the final glucose level by determining a weighted average of the three calculated glucose levels; or
   2. if only two of the three calculated levels are similar within a predefined tolerance level, then calculating the final glucose level by determining a weighted average of only the two similar calculated glucose levels.

12. A non-invasive method of determining the glucose level according to claim 11, further comprising the steps of:
   e. repeating the measurement of one of the parameters;
   f. calculating the corresponding glucose level for the measurement of the parameter in step e herein; and
   g. periodically repeating steps a–d herein to confirm the accuracy of the glucose calculation.

13. A non-invasive method of determining glucose level according to claim 12, wherein steps a–d are repeated after a predetermined amount of time.

14. A non-invasive method of determining glucose level according to claim 12, wherein steps a–d are repeated after a predetermined number of measurements.

15. A non-invasive method of determining glucose level according to claim 11, wherein the three distinct parameters of the body from which glucose level can be calculated are selected from the group consisting of speed of sound though the body, conductivity, heat capacity of the blood, acoustic impedance, electrical/magnetic coefficient, thermal conductivity, elasticity, blood density, specific gravity, polarization coefficient, optical scattering, nuclear magnetic resonance, analyte calculation, blood temperature, body temperature, the effects of thermal waves, the infrared radiation naturally emitted from the body, responses by the tissue to a stimulus, electrical properties, electromotive force and electric current.

16. A non-invasive method of determining glucose level according to claim 11, wherein the weight for each calculated glucose level is based on the reliability of the measurement of the corresponding parameter.

17. A non-invasive method of determining glucose level according to claim 11, wherein, if one of the calculated glucose levels is not within the predefined tolerance level, then checking the remaining two calculated glucose levels to confirm they are within a tighter tolerance range and then calculating the final glucose level by determining the weighted average of only the two similar calculated glucose levels.

18. A non-invasive method of determining glucose level according to claim 11, consisting of the additional steps of: incrementing a counter each time one of the calculated glucose levels is not within the tolerance level; and recalibrating measurement procedure when the counter indicates a predetermined number of times the calculated glucose level was not within the tolerance level.

19. A non-invasive method of determining the glucose level of blood in a patient comprising the steps of:
   a. non-invasively measuring three distinct parameters of the body from which glucose level can be calculated;
   b. calculating the corresponding glucose level for each of the three measurements;
   c. calculating a glucose level by determining a weighted average of the three calculated glucose levels
   d. repeating the measurement of one of the parameters;
   e. calculating the corresponding glucose level for the measurement of the parameter in step d herein; and
   f. periodically repeating steps a–c herein to confirm the accuracy of the glucose calculation.

* * * * *